United States Patent
De Haan (10) Patent No.: US 10,646,167 B2
(45) Date of Patent: May 12, 2020

(54) DEVICE, SYSTEM AND METHOD FOR EXTRACTING PHYSIOLOGICAL INFORMATION

(71) Applicant: KONINKLIJKE PHILIPS N.V., Eindhoven (NL)

(72) Inventor: Gerard De Haan, Helmond (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 471 days.

(21) Appl. No.: 15/279,474

(22) Filed: Sep. 29, 2016

(65) Prior Publication Data

US 2017/0086755 A1 Mar. 30, 2017

Related U.S. Application Data

(60) Provisional application No. 62/234,440, filed on Sep. 29, 2015.

(30) Foreign Application Priority Data

Sep. 29, 2015 (EP) .................................... 15187416

(51) Int. Cl.
*A61B 5/024* (2006.01)
*A61B 5/08* (2006.01)
(Continued)

(52) U.S. Cl.
CPC ............. *A61B 5/7278* (2013.01); *A61B 5/01* (2013.01); *A61B 5/021* (2013.01);
(Continued)

(58) Field of Classification Search
CPC ....... A61B 5/7278; A61B 5/7207; A61B 5/01; A61B 5/021; A61B 5/02405;
(Continued)

(56) References Cited

U.S. PATENT DOCUMENTS

2009/0082642 A1  3/2009  Fine
2013/0271591 A1*  10/2013  Van Leest ............ A61B 5/0064
                                                            348/77

(Continued)

OTHER PUBLICATIONS

De Haan, G., & Van Leest, A. (2014). Improved motion robustness of remote-PPG by using the blood volume pulse signature. Physiological measurement, 35(9), 1913. (Year: 2014).*

(Continued)

*Primary Examiner* — Theodore J Stigell
*Assistant Examiner* — Johnathan Maynard (57) ABSTRACT

A device, system and a method extract physiological information indicative of at least one vital sign of a subject. To provide a high motion robustness, an input interface is configured to obtain at least two detection signals derived from detected electromagnetic radiation transmitted through or reflected from a skin region of a subject. Each detection signal includes wavelength-dependent reflection or transmission information in a different wavelength channel. At least two pulse signals are computed from said at least two detection signals using different signature vectors for the computation of each pulse signal. Quality indicator values are computed for the pulse signals indicating a characteristic of the respective pulse signal. Physiological information indicative of at least one vital sign is derived from the signature vector resulting in the pulse signal with the best quality indicator value and/or from the pulse signal.

15 Claims, 4 Drawing Sheets

(51) Int. Cl.
  A61B 5/145   (2006.01)
  A61B 5/1455  (2006.01)
  A61B 5/00    (2006.01)
  A61B 5/01    (2006.01)
  A61B 5/021   (2006.01)

(52) U.S. Cl.
  CPC ...... *A61B 5/02405* (2013.01); *A61B 5/02416* (2013.01); *A61B 5/0816* (2013.01); *A61B 5/14532* (2013.01); *A61B 5/14551* (2013.01); *A61B 5/7207* (2013.01); *A61B 5/7221* (2013.01); *A61B 5/742* (2013.01); *A61B 5/0075* (2013.01)

(58) Field of Classification Search
  CPC .............. A61B 5/02416; A61B 5/0816; A61B 5/14532; A61B 5/14551; A61B 5/7221; A61B 5/742; A61B 5/0075
  See application file for complete search history.

(56)           References Cited

U.S. PATENT DOCUMENTS

2014/0275825 A1    9/2014  Lisogurski
  2016/0242700 A1*   8/2016  Ferber ................. A61B 5/7278

OTHER PUBLICATIONS

De Haan, G., & Van Leest, A. (2014). Improved motion robustness of remote-PPG by using the blood volume pulse signature. Physiological measurement, 35(9), 1913. (Year: 2014).*

Papageorgiou, A., & de Haan, G. (2014). Adaptive gain tuning for robust remote pulse rate monitoring under changing light conditions. (Year: 2014).*

Verkruysse et al., "Remote plethysmographic imaging using ambient light", Optics Express, 16(26), Dec. 22, 2008, pp. 21434-21445.

Wieringa, et al., "Contactless Multiple Wavelength Photoplethysmographic Imaging: A First Step Toward "SpO2 Camera" Technology," Ann. Biomed. Eng. 33, 1034-1041 (2005).

G. de Haan and A. van Leest, "Improved motion robustness of remote-PPG by using the blood volume pulse signature", Physiol. Meas. 35 1913, 2014.

W. Wang, S. Stuijk and G. de Haan, "Exploiting Spatial Redundancy of Image Sensor for Motion Robust rPPG," in IEEE Transactions on Biomedical Engineering, vol. 62, No. 2, pp. 415-425, Feb. 2015.

Luis F. Corral Martinez; Gonzalo Paez; Marija Strojnik, "Optimal wavelength selection for noncontact reflection photoplethysmography", in Proceedings of SPIE—The International Society for Optical Engineering 8011:304. Aug. 2011.

Castel, et al., "Motion robust remote-PPG in infrared", IEEE, Tr. On Biomedical Engineering, 2015, DOI: 10.1109/TBME.2015.2390261.

Rasoul Yousefi et al In "A Motion-Tolerant Adaptive Algorithm for Wearable Photoplethysmographic Biosensors", 2013 IEEE.

Christopher Dickson In "Heart rate artifact suppression", MS Thesis, Grand Valley State University, 2012.

Jensen, et al., "Independent Component Analysis Applied to Pulse Oximetry in the Estimation of the Arterial Oxygen Saturation (SpO2)—a Comparative Study", Conf Proc IEEE Eng Med Biol Soc. 2009;2009:4039-44.

* cited by examiner

DEVICE, SYSTEM AND METHOD FOR EXTRACTING PHYSIOLOGICAL INFORMATION

CROSS REFERENCE TO RELATED APPLICATIONS

This application claims the benefit of U.S. Provisional Application No. 62/234,440 filed Sep. 29, 2015 and European Application Number 15187416.1 filed Sep. 29, 2015, which are incorporated herein by reference.

FIELD OF THE INVENTION

The present invention relates to a device, system and method for extracting physiological information indicative of at least one vital sign of a subject from detected electromagnetic radiation transmitted through or reflected from a subject, such as a person or animal.

BACKGROUND OF THE INVENTION

Vital signs of a person, for example the heart rate (HR), the respiration rate (RR) or the arterial blood oxygen saturation, serve as indicators of the current state of a person and as powerful predictors of serious medical events. For this reason, vital signs are extensively monitored in inpatient and outpatient care settings, at home or in further health, leisure and fitness settings.

One way of measuring vital signs is plethysmography. Plethysmography generally refers to the measurement of volume changes of an organ or a body part and in particular to the detection of volume changes due to a cardio-vascular pulse wave traveling through the body of a subject with every heartbeat.

Photoplethysmography (PPG) is an optical measurement technique that evaluates a time-variant change of light reflectance or transmission of an area or volume of interest. PPG is based on the principle that blood absorbs light more than surrounding tissue, so variations in blood volume with every heart beat affect transmission or reflectance correspondingly. Besides information about the heart rate, a PPG waveform can comprise information attributable to further physiological phenomena such as the respiration. By evaluating the transmittance and/or reflectivity at different wavelengths (typically red and infrared), the blood oxygen saturation can be determined.

Conventional pulse oximeters (also called contact PPG device herein) for measuring the heart rate and the (arterial) blood oxygen saturation (also called SpO2) of a subject are attached to the skin of the subject, for instance to a fingertip, earlobe or forehead. Therefore, they are referred to as 'contact' PPG devices. A typical pulse oximeter comprises a red LED and an infrared LED as light sources and one photodiode for detecting light that has been transmitted through patient tissue. Commercially available pulse oximeters quickly switch between measurements at a red and an infrared wavelength and thereby measure the transmittance of the same area or volume of tissue at two different wavelengths. This is referred to as time-division-multiplexing. The transmittance over time at each wavelength gives the PPG waveforms for red and infrared wavelengths. Although contact PPG is regarded as a basically non-invasive technique, contact PPG measurement is often experienced as being unpleasant and obtrusive, since the pulse oximeter is directly attached to the subject and any cables limit the freedom to move and might hinder a workflow.

Fast and reliable detection and analysis of a pulse signal and oxygen saturation level (SpO2) is one of the most important activities in many healthcare applications, which becomes crucial if a patient is in a critical condition, and therefore, the measurement is vulnerable to any sort of artifacts. Further, also in healthy individuals the signals are small and therefore easily distorted by motion of the subject.

Modern photoplethysmography sensors typically fail when the subject moves and the vital signs monitoring is often interrupted. For instance, contact finger pulse oximeters (based on transmissive PPG) are vulnerable to motion of a hand, and fails in case of centralization of a patient due to lower blood volumes on body peripherals. Contact forehead pulse oximeter sensors (using a reflective PPG measurement mode) are supposed to be more robust to a centralization effect. However, the accuracy, robustness and responsiveness of a forehead sensor depends heavily on correct positioning of a sensor on a forehead and proper pressure applied to a skin (too tight application of a sensor might reduce a local blood pulsatility, too loose application might lead to non-reliable measurements due to motion artifacts and/or venous pulsatility).

Recently, non-contact, remote PPG (rPPG) devices (also called camera rPPG device herein) for unobtrusive measurements have been introduced. Remote PPG utilizes light sources or, in general radiation sources, disposed remotely from the subject of interest. Similarly, also a detector, e.g., a camera or a photo detector, can be disposed remotely from the subject of interest. Therefore, remote photoplethysmographic systems and devices are considered unobtrusive and well suited for medical as well as non-medical everyday applications. However, remote PPG devices typically achieve a lower signal-to-noise ratio.

Verkruysse et al., "Remote plethysmographic imaging using ambient light", Optics Express, 16(26), 22 Dec. 2008, pp. 21434-21445 demonstrates that photoplethysmographic signals can be measured remotely using ambient light and a conventional consumer level video camera, using red, green and blue color channels.

Wieringa, et al., "Contactless Multiple Wavelength Photoplethysmographic Imaging: A First Step Toward "SpO2 Camera" Technology," Ann Biomed. Eng. 33, 1034-1041 (2005), discloses a remote PPG system for contactless imaging of arterial oxygen saturation in tissue based upon the measurement of plethysmographic signals at different wavelengths. The system comprises a monochrome CMOS-camera and a light source with LEDs of three different wavelengths. The camera sequentially acquires three movies of the subject at the three different wavelengths. The pulse rate can be determined from a movie at a single wavelength, whereas at least two movies at different wavelengths are required for determining the oxygen saturation. The measurements are performed in a darkroom, using only one wavelength at a time.

Using PPG technology, vital signs can be measured, which are revealed by minute light absorption changes in the skin caused by the pulsating blood volume, i.e. by periodic color changes of the human skin induced by the blood volume pulse. As this signal is very small and hidden in much larger variations due to illumination changes and motion, there is a general interest in improving the fundamentally low signal-to-noise ratio (SNR). There still are demanding situations, with severe motion, challenging environmental illumination conditions, or high required accuracy of the application, where an improved robustness and accuracy of the vital sign measurement devices and methods is required, particularly for the more critical healthcare applications.

In summary, Video Health Monitoring (heart rate, respiration rate, SpO2, actigraphy, delirium etc.) is a promising emerging field. Its inherent unobtrusiveness has distinct advantages for patients with fragile skin, or in need of long-term vital signs monitoring, such as NICU patients, patients with extensive burns, or COPD patients who have to be monitored at home during sleep. In other settings such as in a general ward or emergency room, the comfort of contactless monitoring is still an attractive feature. However, while a promising new field, many challenges have to be overcome, in particular designing the system to be robust to movements of the patient is currently one of the main challenges. Further, it is desired to have reliable measurements in case of low pulsatility (e.g. for neonates, at low temperatures). In general, the known methods become unreliable with low SNR, which shall be improved.

A major problem with known methods is their sensitivity for subject motion and low SNR. The reason for this is that the vital signs manifest themselves as small color variations of the skin that are detected by the camera or contact sensor. Subject motion, however, leads easily to much larger variations in the detected signals and recovering the vital sign from these distorted signals is the main issue in the known methods.

G. de Haan and A. van Leest, "Improved motion robustness of remote-PPG by using the blood volume pulse signature", Physiol. Meas. 35 1913, 2014 describes that the different absorption spectra of arterial blood and bloodless skin cause the variations to occur along a very specific vector in a normalized RGB-space. The exact vector can be determined for a given light-spectrum and transfer-characteristics of the optical filters in the camera. It is shown that this 'signature' can be used to design an rPPG algorithm with a much better motion robustness than the recent methods based on blind source separation, and even better than the chrominance-based methods published earlier.

W. Wang, S. Stuijk and G. de Haan, "Exploiting Spatial Redundancy of Image Sensor for Motion Robust rPPG," in IEEE Transactions on Biomedical Engineering, vol. 62, no. 2, pp. 415-425, February 2015 discloses a framework to improve the motion robustness of rPPG based on the observation that a camera can simultaneously sample multiple skin regions in parallel, and each of them can be treated as an independent sensor for pulse measurement. The spatial redundancy of an image sensor can thus be exploited to distinguish the pulse signal from motion-induced noise. To this end, the pixel-based rPPG sensors are constructed to estimate a robust pulse signal using motion-compensated pixel-to-pixel pulse extraction, spatial pruning, and temporal filtering.

Luis F. Corral Martinez; Gonzalo Paez; Marija Strojnik, "Optimal wavelength selection for noncontact reflection photoplethysmography", in Proceedings of SPIE—The International Society for Optical Engineering 8011:304. August 2011 describes backscattered signals from human forehead for wavelengths from 380 to 980 nm. The results reveal bands with strong pulsatile signals that carry useful information. Those bands are described as the most suitable wavelengths in the visible and NIR regions from which heart and respiratory rate parameters can be derived using long distance non-contact reflection photoplethysmography analysis. The latter results show the feasibility of a novel technique for remote detection of vital signs in humans. This technique, which may include morphological analysis or maps of tissue oxygenation, is a further step to real non-invasive remote monitoring of patients.

SUMMARY OF THE INVENTION

It is an object of the present invention to provide a device, system and a method for extracting physiological information indicative of at least one vital sign of a subject, which provide an increased robustness of the obtained vital sign(s) with respect to motion and low SNR.

In a first aspect of the present invention, a device for extracting physiological information indicative of at least one vital sign of a subject is presented, the device comprising:

an input interface configured to obtain at least two detection signals derived from detected electromagnetic radiation transmitted through or reflected from a skin region of a subject, wherein each detection signal comprises wavelength-dependent reflection or transmission information in a different wavelength channel, a pulse signal computation unit configured to compute at least two pulse signals from said at least two detection signals using different signature vectors for the computation of each pulse signal, said signature vectors providing an expected relative strength of the pulse signal in the at least two detection signals, wherein the computation of a pulse signal involves a weighted combination of the at least two detection signals using weights selected such that the resulting pulse signal correlates with the original detection signals as indicated by the respective signature vector, a quality indicator computation unit configured to compute quality indicator values for said pulse signals indicating a characteristic of the respective pulse signal, and a processing unit configured to derive physiological information indicative of at least one vital sign from the signature vector that results in the pulse signal with the best quality indicator value and/or from said pulse signal.

In a further aspect of the present invention, a system for extracting physiological information indicative of at least one vital sign of a subject from detected electromagnetic radiation transmitted through or reflected from a subject is presented, the system comprising:

a detector configured to detect electromagnetic radiation transmitted through or reflected from a skin region of a subject and to derive at least two detection signals from the detected electromagnetic radiation, wherein each detection signal comprises wavelength-dependent reflection or transmission information in a different wavelength channel, a device as disclosed herein for extracting physiological information.

In yet further aspects of the present invention, there are provided a corresponding method, a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, system, computer program and medium have similar and/or identical preferred embodiments as the claimed device and as defined in the dependent claims.

The known SpO2 measurement uses a ratio of the PPG amplitude in red and IR. Particularly the red PPG signal is very small. With the known method, the amplitude of the red PPG signal is overestimated because it includes noise. In contrast, the device and method according to the present invention do not measure the amplitude, but rather the signature (e.g. a $P_{bv}$ vector) that gives the best SNR. Even if this SNR is low, it can still be measured as the best (using a lower limit to the SNR that can be dealt with).

As explained above, a PPG signal results from variations of the blood volume in the skin. Hence the variations give a characteristic pulsatility "signature" when viewed in different spectral components of the reflected/transmitted light. This "signature is basically resulting as the contrast (difference) of the absorption spectra of the blood and that of the blood-less skin tissue. If the detector, e.g. a camera or sensor, has a discrete number of color channels, each sensing a particular part of the light spectrum, then the relative pulsatilities in these channels can be arranged in a "signature vector", also referred to as the "normalized blood-volume vector", $P_{bv}$. It has been shown in G. de Haan and A. van Leest, "Improved motion robustness of remote-PPG by using the blood volume pulse signature", Physiol. Meas. 35 1913, 2014, which is herein incorporated by reference, that if this signature vector is known then a motion-robust pulse signal extraction on the basis of the color channels and the signature vector is possible. For the quality of the pulse signal it is essential though that the signature is correct, as otherwise the known methods mixes noise into the output pulse signal in order to achieve the prescribed correlation of the pulse vector with the normalized color channels as indicated by the signature vector.

Details of the $P_{bv}$ method and the use of the normalized blood volume vector (called "predetermined index element having a set orientation indicative of a reference physiological information") have also been described in US 2013/0271591 A1, which details are also herein incorporated by reference.

Hence, it is proposed according to the present invention that quality indicator values are computed for the pulse signals computed from the detection signals (also called color signals or color channels) using different signature vectors, said quality indicator values indicating a characteristic of the respective pulse signal, and that physiological information indicative of at least one vital sign is derived from the signature vector that results in the pulse signal with the best quality indicator value and/or from said pulse signal, i.e. the pulse signal with the best quality indicator value.

Hereby, vital signs like for example SpO2, CO, CO2, and bilirubin are preferably derived from said determined signature vector. However, the pulse signal with the best quality indicator value itself is also an interesting vital sign that the proposed device can output. Even further, the pulse-rate, interbeat interval, or heart-rate variability can be derived from said pulse signal. This pulse signal is more robust in case of varying SpO2 than a pulse signal obtained with a fixed signature vector.

The approach proposed by the present invention may also be understood as a quality guided walk along a defined line in color space, where the line depends on the choice of optical filters (wavelengths). The signature vector is dynamically adapted in the color space to further reduce the influence of motion in each specific measurement.

In an embodiment said pulse signal computation unit is configured to use a fixed set of different signature vectors and said processing unit is configured to filter the time sequence of signature vectors that resulted in the pulse signal with the best quality indicator value to obtain a filtered signature vector from which the physiological information is derived. According to this embodiment the set of different signature vectors is fixed, i.e. each signature vector corresponds to a discrete vital signs value, e.g. a SpO2 value (in a range between 60% and 100%, e.g. covered by 10 signature vectors). Further, the filtered signature vector (having an increased resolution, e.g. SpO2 resolution) is used to derive the output vital sign, using the fact that the signature vector one-on-one corresponds to vital signs value, e.g. an SpO2 value.

In another embodiment the device further comprises a signature adaptation unit for adapting one or more of the different signature vectors in a direction that depends on which pulse signal yields the best quality indicator value. According to this embodiment a signature value is adapted (i.e. updated) in a direction (e.g. an update value is increased or decreased) that depends on which pulse signal (computed using one of the signature values) yields the best quality indicator value. Hence, a recursive/iterative option is used according to this embodiment. Generally, the set of signature vectors may contain only two signature vectors, but more is possible.

Thus, this embodiment provides an adaptation scheme of the signature vector in a PPG sensor as disclosed in the above cited paper of de Haan and van Leest such that the signature automatically converges to the correct signature vector. On top of improving the motion and noise robustness of the pulse signal, a further advantage is that the signature vector carries all relevant information concerning the composition of the blood (e.g. of SpO2, CO, CO2, bilirubin).

In case of partly adapting the set of signature values the recursive/iterative option may be extended with a fixed signature vector that is always tested. The set may thus contain two adapted signature vectors, and e.g. one up to three fixed signature vectors that may speed up recovery if the recursive approach got "off-track", e.g. by excessive noise.

In another preferred embodiment said signature adaptation unit is configured to use a reference signature vector to obtain at least two signature vectors based on said quality indicator values and wherein said pulse signal computation unit is configured to compute said pulse signals from said detection signal for said at least two signature vectors such that a pulse signal correlates with said at least two detection signals in a ratio determined by the corresponding signature vector. The reference signature vector is preferably fixed and predetermined. It may e.g. be measured once for a given configuration (camera, light-source) on a healthy individual (i.e. with a healthy SpO2 around 97%). It is also possible to use a phantom for this. The phantom can be a computer monitor displaying a surface with the color variations typically seen in healthy skin. The reference signature vector does not have to correspond though to the signature vector of a healthy individual. It is also possible to take a vector that corresponds to another SpO2 value, e.g. of 80%. As long as the reference signature vector is within the range that may occur (between 70% and 100% SpO2), it may serve as an initial estimate and the method according to the present invention will converge towards the actual signature value of the subject monitored.

Preferably, said signature adaptation unit is configured to adapt a reference normalized blood volume pulse vector as reference signature vector to obtain the at least two signature vectors.

There are different options to determine the quality indicator values. In an embodiment said quality indicator computation unit is configured to compute the spectrum of normalized pulse signals, in particular over a sliding time window, and to use an amplitude of the highest peak in a range, in particular of typical pulse frequencies, as the quality indicator for said pulse signal. In another embodiment, said quality indicator computation unit is configured to compute pulse signals in a sliding time window and to define an amplitude of the highest peak in the range of the pulse frequencies of the spectrum, divided by the energy over the full frequency range (which may also be the range of possible pulse frequencies), as the quality indicator for said pulse signal.

The signature adaptation unit may be configured to compare said quality indicator values to increase or decrease a counter depending on the sign of the comparison and to use the counter value together with a predetermined update vector and the reference signature vector to compute the at least two signature vectors. The update vector is generally predetermined. For instance, if a signature vector describing the relative pulsatilities in the detection signals for 100% SpO2 is used as $P_{bv2}$ and from that the signature vector $P_{bv3}$ for e.g. 80% SpO2 is subtracted, a fraction of this difference vector may be used as update vector.

The pulse signal computation unit may further be configured to add noise to one or more of the said at least two detection signals, in particular to one or more normalized and DC-free detection signals before computing said pulse signals therefrom. Adding some noise to the color channels improves the performance, in particular in case the skin area is large and there is little observation or motion-induced noise. The advantageous effect is that the estimation of all the vital signs actually profits from noise (e.g. motion) as the optimal signature is clearest in the presence of a disturbance. In a very noise-free situation, almost all signature vectors ($P_{bv}$s) may lead to a clean pulse signal so that it may become hard to find the optimum.

In a practical implementation said pulse signal computation unit is configured to compute said pulse signals $S_1$, $S_2$ by computing a covariance matrix $Q=C_n C_n^T$ of normalized DC-free detection signals $C_n$ over a time window and find the weights $W_x$ to compute a pulse signal $S_x=\vec{W}_x C_n$ as $\vec{W}_x = k \vec{P}_{bv} Q^{-1}$ where k is chosen to make $\|\vec{W}_x\|=1$ and $x \in \{1, 2\}$. It shall be noted here that the weights and the $P_{bv}$s are different for the two pulse signals obtained from the same detection signals $C_n$.

The proposed device may further comprise a control signal computation unit configured to compute a control signal from said quality indicator values, wherein said signature adaptation unit is configured to adapt said reference signature vector based on said control signal to obtain at least two signature vectors. The control signal can e.g. be +1 or −1 (e.g. to increase or decrease a counter), depending which of the two signature vectors is best. The sign should be selected such that the process converges towards the correct estimate.

In this embodiment said signature adaptation unit is preferably configured to compute the at least two signature vectors by adding update vectors (CS−1)·$\vec{U}$ and (CS+1)·$\vec{U}$ to the reference signature vector, wherein said control signal computation unit is configured to increase the control signal CS in case the quality indicator value of the second pulse signal is larger than the quality indicator value of the first pulse signal and vice versa.

The detector of the proposed system may be configured in different ways, in particular to detect detection signals at different wavelengths, preferably depending on the kind of application and the system configuration. In preferred embodiment it is configured to derive detection signals at wavelengths around 650 nm, 810 nm and 900 nm, or at wavelengths around 760 nm, 800 nm and 840 nm, or at wavelengths around 475 nm, 550 nm and 650 nm, or at wavelengths around 650 nm and 800 nm, or at wavelengths around 660 nm, 760 nm, 800 nm and 840 nm. Generally, each detection signal comprises wavelength-dependent reflection or transmission information in a different wavelength channel, which means that the different 'wavelength channels' have a different sensitivity for wavelengths. Hence, they can be sensitive for the same wavelengths, but then the relative sensitivities should be different. In other words, optical filters, which may be used for sensing, may be (partially) overlapping, but should be different.

In general, the at least two signal channels (detection signals) are selected from a wavelength interval between 300 nm and 1000 nm, in particular represent the wavelength portions corresponding to red, green and blue light. This is particularly used when the PPG signals are obtained from image signals acquired by a (e.g. conventional) video camera and when the above mentioned principles of remote PPG are used for deriving one or more vital signs. In other embodiments infrared light may also be used in addition or instead of another color channel. For instance, for night-time applications one or more infrared wavelengths may be used in addition or alternatively.

Generally, the interaction of electromagnetic radiation, in particular light, with biological tissue is complex and includes the (optical) processes of (multiple) scattering, backscattering, absorption, transmission and (diffuse) reflection. The term "reflect" as used in the context of the present invention is not to be construed as limited to specular reflection but comprises the afore-mentioned types of interaction of electromagnetic radiation, in particular light, with tissue and any combinations thereof.

The term "vital sign" as used in the context of the present invention refers to a physiological parameter of a subject (i.e. a living being) and derivative parameters. In particular, the term "vital sign" comprises blood volume pulse signal, heart rate (HR) (sometimes also called pulse rate), heart rate variability (pulse rate variability), pulsatility strength, perfusion, perfusion indicator, perfusion variability, Traube Hering Mayer waves, respiratory rate (RR), skin temperature, blood pressure, a concentration of a substance in blood and/or tissue, such as (arterial) blood oxygen saturation or glucose level. Furthermore, "vital sign" generally includes health indications obtained from the shape of the PPG signal (e.g. shape may say something about partial arterial blockage (e.g. shape obtained from PPG signals of the hand gets more sinusoidal when applying a blood-pressure cuff on the arm), or about the skin thickness (e.g. a PPG signal from the face is different than from the hand), or may be even about the temperature, etc.).

The term "vital sign information" as used in the context of the present invention comprises the one or more measured vital signs as defined above. Furthermore, it comprises data referring to a physiological parameter, corresponding waveform traces or data referring to a physiological parameter of a time that can serve for subsequent analysis.

For obtaining a vital sign information signal of the subject the data signals of skin pixel areas within the skin area are evaluated. Here, a "skin pixel area" means an area comprising one skin pixel or a group of adjacent skin pixels, i.e. a data signal may be derived for a single pixel or a group of skin pixels.

The detector for detecting electromagnetic radiation transmitted through or reflected from a skin region of a subject and for deriving detection data from the detected electromagnetic radiation may be implemented in various ways. In one embodiment the detector comprises a plethysmography sensor configured for being mounted to a skin portion of the subject for acquiring photoplethysmography signals. Such a sensor may e.g. be an optical plethysmography sensor mounted to a finger or earlobe or a sensor arranged within a wristband or wristwatch.

In another embodiment the detector may comprise an imaging unit for acquiring a sequence of image frames of the subject over time, from which photoplethysmography signals can be derived using the principle of remote PPG. The data stream may thus comprise a sequence of image frames or, more precisely, a series of image frames comprising spectral information. For instance, RGB-images comprising color information can be utilized. However, also frames representing infrared (IR) and red (R) information can form the sequence of frames. The image frames can represent the observed subject and further elements.

The present invention achieves motion robust SpO2 measurements with a Vital Signs Camera, but also results in an improved motion robust pulse signal, an improved pulse rate, possibly an improved serum bilirubin, CO2 and CO estimation (essentially all PPG-based information can be made more robust). Finally, the invention is equally suitable to improve motion robustness of contact oximeters.

In a further aspect the present invention a device for extracting physiological information indicative of at least one vital sign of a subject is presented, said device comprising a processor configured to carry out the steps of:

obtaining at least two detection signals derived from detected electromagnetic radiation transmitted through or reflected from a skin region of a subject, wherein each detection signal comprises wavelength-dependent reflection or transmission information in a different wavelength channel, computing pulse signals from said at least two detection signals, computing quality indicator values for said pulse signals indicating a characteristic of the respective pulse signal, and deriving physiological information indicative of at least one vital sign from the signature vector that results in the pulse signal with the best quality indicator value and/or from said pulse signal.

BRIEF DESCRIPTION OF THE DRAWINGS

These and other aspects of the invention will be apparent from and elucidated with reference to the embodiments described hereinafter. In the following drawings.

DETAILED DESCRIPTION OF THE INVENTION

Figure 1:
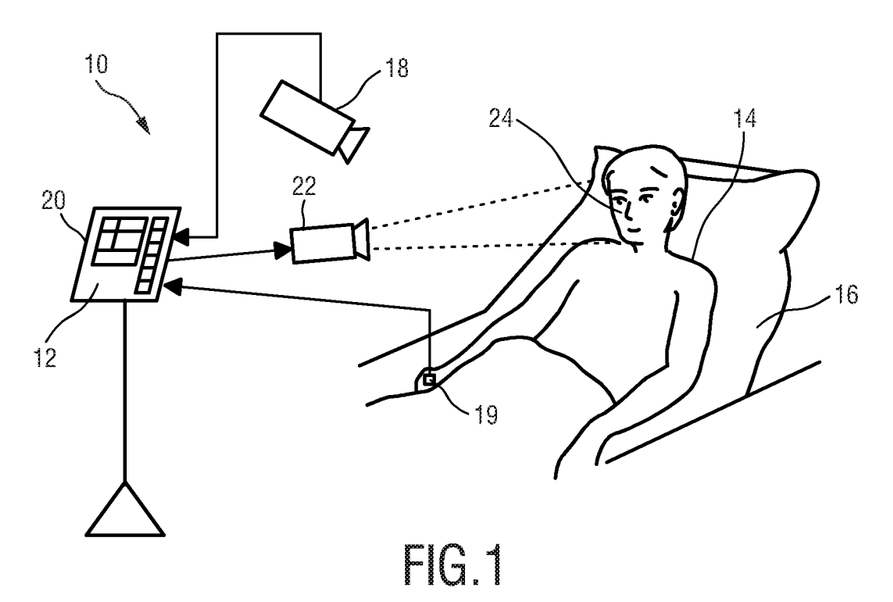
FIG. 1 shows a schematic diagram of a system according to the present invention.

FIG. 1 shows a schematic diagram of a system 10 according to the present invention including a device 12 for extracting physiological information indicative of at least one vital sign of a subject 14 from detected electromagnetic radiation transmitted through or reflected from a subject. The subject 14, in this example is a patient, lies in a bed 16, e.g. in a hospital or other healthcare facility, but may also be a neonate or premature infant, e.g. lying in an incubator, or person at home or in a different environment.

There exist different embodiments for a detector for detecting electromagnetic radiation transmitted through or reflected from a subject, which may alternatively (which is preferred) or together be used. In the embodiment of the system 10 two different embodiments of the detector are shown and will be explained below. Both embodiments of the detector are configured for deriving at least two detection signals from the detected electromagnetic radiation, wherein each detection signal comprises wavelength-dependent reflection or transmission information in a different wavelength channel. Hereby, optical filters used are preferably different, but can be overlapping. It is sufficient if their wavelength-dependent transmission is different.

In one embodiment the detector comprises a camera 18 (also referred to as imaging unit, or as camera-based or remote PPG sensor) including a suitable photosensor for (remotely and unobtrusively) capturing image frames of the subject 14, in particular for acquiring a sequence of image frames of the subject 14 over time, from which photoplethysmography signals can be derived. The image frames captured by the camera 18 may particularly correspond to a video sequence captured by means of an analog or digital photosensor, e.g. in a (digital) camera. Such a camera 18 usually includes a photosensor, such as a CMOS or CCD sensor, which may also operate in a specific spectral range (visible, IR) or provide information for different spectral ranges. The camera 18 may provide an analog or digital signal. The image frames include a plurality of image pixels having associated pixel values. Particularly, the image frames include pixels representing light intensity values captured with different photosensitive elements of a photosensor. These photosensitive elements may be sensitive in a specific spectral range (i.e. representing a specific color). The image frames include at least some image pixels being representative of a skin portion of the subject. Thereby, an image pixel may correspond to one photosensitive element of a photo-detector and its (analog or digital) output or may be determined based on a combination (e.g. through binning) of a plurality of the photosensitive elements.

In another embodiment the detector comprises one or more optical photoplethysmography sensor(s) 19 (also referred to as contact PPG sensor(s)) configured for being mounted to a skin portion of the subject 14 for acquiring photoplethysmography signals. The PPG sensor(s) 19 may e.g. be designed in the form of a finger-clip for measuring the blood oxygen saturation or a heart rate sensor for measuring the heart rate, just to name a few of all the possible embodiments.

When using a camera 18 the system 10 may further optionally comprises a light source 22 (also called illumination source), such as a lamp, for illuminating a region of interest 24, such as the skin of the patient's face (e.g. part of the cheek or forehead), with light, for instance in a predetermined wavelength range or ranges (e.g. in the red, green and/or infrared wavelength range(s)). The light reflected from said region of interest 24 in response to said illumination is detected by the camera 18. In another embodiment no dedicated light source is provided, but ambient light is used for illumination of the subject 14. From the reflected light only light in a desired wavelength ranges (e.g. green and red or infrared light, or light in a sufficiently large wavelength range covering at least two wavelength channels) may be detected and/or evaluated.

The device 12 is further connected to an interface 20 for displaying the determined information and/or for providing medical personnel with an interface to change settings of the device 12, the camera 18, the PPG sensor(s) 19, the light source 22 and/or any other parameter of the system 10. Such an interface 20 may comprise different displays, buttons, touchscreens, keyboards or other human machine interface means.

A system 10 as illustrated in FIG. 1 may, e.g., be located in a hospital, healthcare facility, elderly care facility or the like. Apart from the monitoring of patients, the present invention may also be applied in other fields such as neonate monitoring, general surveillance applications, security monitoring or so-called live style environments, such as fitness equipment, a wearable, a handheld device like a smartphone, or the like. The uni- or bidirectional communication between the device 12, the camera 18, the PPG sensor(s) 19 and the interface 20 may work via a wireless or wired communication interface. Other embodiments of the present invention may include a device 12, which is not provided stand-alone, but integrated into the camera 18 or the interface 20.

There exist several known methods to obtain a pulse signal S from detection signals $C_n$, said methods being referred to as ICA, PCA, $P_{BV}$, CHROM, and ICA/PCA guided by $P_{BV}$/CHROM, which have also been described in the above cited paper of de Haan and van Leest. These methods can be interpreted as providing the pulse signal S as a mixture of different wavelength channels, e.g. red, green and blue signals from a color video camera, but they differ in the way to determine the optimal weighting scheme. In these methods the resulting weights are aimed at a mixture in which the distortions disappear, i.e. the "weighting vector" is substantially orthogonal to the main distortions usually caused by subject motion and/or illumination variations.

In the following some basic considerations with respect to the $P_{bv}$ method shall be briefly explained.

The beating of the heart causes pressure variations in the arteries as the heart pumps blood against the resistance of the vascular bed. Since the arteries are elastic, their diameter changes in sync with the pressure variations. These diameter changes occur even in the smaller vessels of the skin, where the blood volume variations cause a changing absorption of the light.

The unit length normalized blood volume pulse vector (also called signature vector) is defined as $P_{bv}$, providing the relative PPG-strength in the red, green and blue camera signal, i.e.

$$\vec{P}_{bv} = \frac{[\sigma(\vec{R}_n), \sigma(\vec{G}_n), \sigma(\vec{B}_n)]}{\sqrt{\sigma^2(\vec{R}_n) + \sigma^2(\vec{G}_n) + \sigma^2(\vec{B}_n)}}$$

with $\sigma$ indicating the standard deviation.

To quantify the expectations, the responses $H_{red}(w)$, $H_{green}(w)$ and $H_{blue}(w)$ of the red, green and blue channel, respectively, were measured as a function of the wavelength w, of a global-shutter color CCD camera 1, the skin reflectance of a subject, $\rho_s(w)$, and used an absolute PPG-amplitude curve PPG(w). From these curves, shown e.g. in FIG. 2 of the above cited paper of de Haan and van Leest, the blood volume pulse vector $P_{bv}$ is computed as:

$$\vec{P}_{bv}^T = \begin{bmatrix} \frac{\int_{w=400}^{700} H_{red}(w)I(w)PPG(w)\,dw}{\int_{w=400}^{700} H_{red}(w)I(w)\rho_s(w)\,dw} \\ \frac{\int_{w=400}^{700} H_{green}(w)I(w)PPG(w)\,dw}{\int_{w=400}^{700} H_{green}(w)I(w)\rho_s(w)\,dw} \\ \frac{\int_{w=400}^{700} H_{blue}(w)I(w)PPG(w)\,dw}{\int_{w=400}^{700} H_{blue}(w)I(w)\rho_s(w)\,dw} \end{bmatrix}$$

which, using a white, halogen illumination spectrum I(w), leads to a normalized $P_{bv}$=[0.27, 0.80, 0.54]. When using a more noisy curve the result may be $P_{bv}$=[0.29, 0.81, 0.50].

The blood volume pulse predicted by the used model corresponds reasonably well to an experimentally measured normalized blood volume pulse vector, $P_{bv}$=[0.33, 0.78, 0.53] found after averaging measurements on a number of subjects under white illumination conditions. Given this result, it was concluded that the observed PPG-amplitude, particularly in the red, and to a smaller extent in the blue camera channel, can be largely explained by the crosstalk from wavelengths in the interval between 500 and 600 nm. The precise blood volume pulse vector depends on the color filters of the camera, the spectrum of the light and the skin-reflectance, as the model shows. In practice the vector turns out to be remarkably stable though given a set of wavelength channels (the vector will be different in the infrared compared to RGB-based vector).

It has further been found that the relative reflectance of the skin, in the red, green and blue channel under white illumination does not depend much on the skin-type. This is likely because the absorption spectra of the blood-free skin is dominated by the melanin absorption. Although a higher melanin concentration can increase the absolute absorption considerably, the relative absorption in the different wavelengths remains the same. This implies an increase of melanin darkens the skin, but hardly changes the normalized color of the skin. Consequently, also the normalized blood volume pulse $P_{bv}$ is quite stable under white illumination. In the infrared wavelengths the influence of melanin is further reduced as its maximum absorption occurs for short wavelengths (UV-light) and decreases for longer wavelengths.

The stable character of $P_{bv}$ can be used to distinguish color variations caused by blood volume change from variations due to alternative causes, i.e. the stable $P_{bv}$ can be used as a "signature" of blood volume change to distinguish their color variations. The known relative pulsatilities of the color channels $P_{bv}$ can thus be used to discriminate between the pulse-signal and distortions. The resulting pulse signal S using known methods can be written as a linear combination (representing one of several possible ways of "mixing") of the individual DC-free normalized color channels:

$$S = WC_n$$

with $WW^T=1$ and where each of the three rows of the 3×N matrix $C_n$ contains N samples of the DC-free normalized red, green and blue channel signals $R_n$, $G_n$ and $B_n$, respectively, i.e.:

$$\vec{R}_n = \frac{1}{\mu(\vec{R})}\vec{R} - 1, \vec{G}_n = \frac{1}{\mu(\vec{G})}\vec{G} - 1, \vec{B}_n = \frac{1}{\mu(\vec{B})}\vec{B} - 1.$$

Here the operator μ corresponds to the mean. Key difference between the different methods is in the calculation of the weighting vector W. In one method, the noise and the PPG signal may be separated into two independent signals built as a linear combination of two color channels. One combination approximated a clean PPG signal, the other contained noise due to motion. As an optimization criterion the energy in the pulse signal may be minimized. In another method a linear combination of the three color channels may be used to obtain the pulse signal. In still further methods, the ICA or the PCA may be used to find this linear combination. Since it is a priori unknown which weighted color signal is the pulse signal all of them used the periodic nature of the pulse signal as the selection criterion.

The $P_{BV}$ method generally obtains the mixing coefficients using the blood volume pulse vector as basically described in US 2013/271591 A1 and the above cited paper of de Haan and van Leest. The best results are obtained if the bandpassed filtered versions of $R_n$, $G_n$ and $B_n$ are used. According to this method the known direction of $P_{bv}$ is used to discriminate between the pulse signal and distortions. This not only removes the assumption (of earlier methods) that the pulse is the only periodic component in the video, but also eliminates assumptions on the orientation of the distortion signals. To this end, it is assumed as before that the pulse signal is built as a linear combination of normalized color signals. Since it is known that the relative amplitude of the pulse signal in the red, green and blue channel is given by $P_{bv}$, the weights, $W_{PBV}$, are searched that give a pulse signal S, for which the correlation with the color channels $R_n$, $G_n$, and $B_n$ equals $P_{bv}$ $$\vec{S}C_n^T = k\vec{P}_{bv} \Leftrightarrow \vec{W}_{PBV}C_nC_n^T = k\vec{P}_{bv}, \quad (1)$$

and consequently the weights determining the mixing are determined by $$\vec{W}_{PBV} = k\vec{P}_{bv}Q^{-1} \text{ with } Q = C_nC_n^T, \quad (2)$$

and the scalar k is determined such that $W_{PBV}$ has unit length. It is concluded that the characteristic wavelength dependency of the PPG signal, as reflected in the normalized blood volume pulse, $P_{bv}$, can be used to estimate the pulse signal from the time-sequential RGB pixel data averaged over the skin area. This algorithm is referred to as the $P_{bv}$ method.

Hence, as explained above, a pulse signal S1, S2 results as a weighted sum of the at least two detection signals $C_n$. Since all detection signals $C_n$ contain the pulse and different levels of (common) noise, the weighting (of the detection signals to obtain the pulse signal) can lead to a pure noise-free pulse. This is why ICA and PCA can be used to separate noise and pulse. According to the present invention this is done differently.

According to the present invention it is assumed that the relative strength (defined by the signature vector (e.g. $P_{bv}$ vector), which contains these relative pulsatilities) of the pulse is known in all detection signals $C_n$ (which is true if the desired vital sign information, e.g. the SpO2, were known, which is not the case since this is the parameter that is searched for). If the weights are chosen correctly, the correlation of the resulting pulse with the individual detection signals $C_n$ are exactly these relative strengths of the pulse in detection signals $C_n$. Now, if the vital sign information (e.g. the SpO2) is wrong or unknown, the result will be a pulse signal with a relatively poor SNR (i.e. a poor quality indicator). By choosing the signature vector (e.g. $P_{bv}$ vector) such that it gives the best SNR (i.e. the best quality indicator), the algorithm provides that it gets closer to knowing the correct vital sign information (e.g. the SpO2).

Figure 2:
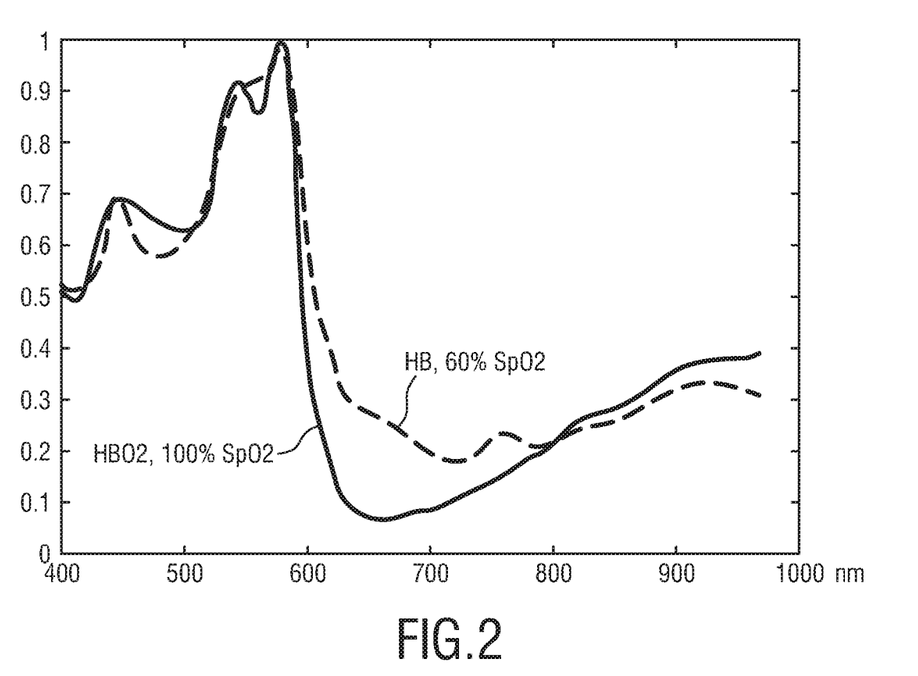
FIG. 2 shows a diagram of the absorption spectrum of blood.

FIG. 2 shows a diagram of the absorption spectrum of blood (for SpO2=100% and SpO2=60%). As can be seen, the absorption spectrum of blood depends on the oxygen saturation. If a detection unit, such as a camera or contact sensor, samples this spectrum, e.g. around 650 nm, 810 nm and 900 nm, the signature vector Pbv has 3 components, and they depend on the SpO2. This is exploited according to the present invention.

Figure 3:
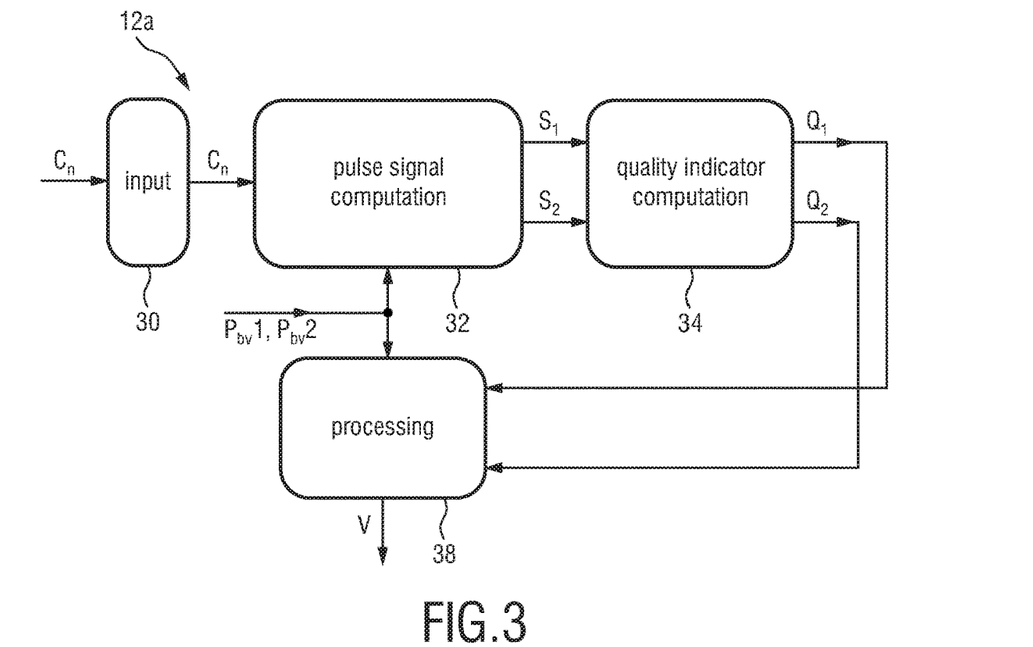
FIG. 3 shows a schematic diagram of a first embodiment of a device according to the present invention.

FIG. 3 shows a more detailed schematic illustration of a first embodiment 12a of the device 12 according to the present invention. The device 12a comprises an input interface 30 for obtaining at least two detection signals $C_n$ derived from detected electromagnetic radiation transmitted through or reflected from a skin region of the subject 14. The data stream of detection data, i.e. the detection signals $C_n$, is e.g. provided by the camera 18 and/or one or more PPG sensor(s) 19, wherein each detection signal comprises wavelength-dependent reflection or transmission information in a different wavelength channel.

A pulse signal computation unit 32 computes at least two pulse signals $S_1$, $S_2$ from said at least two detection signals $C_n$ using different signature vectors $P_{bv}1$, $P_{bv}2$, in particular normalized blood-volume vectors ($P_{bv}$), for the computation of each pulse signal. This step is explained in detail in the above cited paper of de Haan and van Leest or in M. van Gastel, S. Stuijk and G. de Haan, "Motion robust remote-PPG in infrared", IEEE, Tr. On Biomedical Engineering, 2015, DOI: 10.1109/TBME.2015.2390261, which explanations shall not be described here in much detail, but are incorporated herein by reference.

In particular, the different signature vectors $P_{bv}1$, $P_{bv}2$ used for the computation of each pulse signal provide an expected relative strength of the pulse signal $S_1$, $S_2$ in the at least two detection signals $C_n$. The computation of a pulse signal $S_1$, $S_2$ involves a weighted combination of the at least two detection signals $C_n$ using weights selected such that the resulting pulse signal $S_1$, $S_2$ correlates with the original detection signals $C_n$ as indicated by the respective signature vector $P_{bv}1$, $P_{bv}2$.

A quality indicator computation unit 34 computes quality indicator values $Q_1$, $Q_2$ for said pulse signals $S_1$, $S_2$ indicating a characteristic of the respective pulse signal.

A processing unit 38 derives physiological information V indicative of at least one vital sign from the signature vector that results in the pulse signal with the best quality indicator value $Q_1$, $Q_2$. By knowing which signature vector has the best quality indicator value the processing unit 38 can determine the physiological information V, e.g. a vital sign of the subject such as the subject's SpO2 value, since it is determined by the signature vector that gives the best quality pulse signal. Alternatively, it can compute the pulse rate or the inter-beat-interval, the heart rate variability, or another characteristic of the pulse signal with the best quality indicator value Q as the vital sign.

In this context, the "best" quality indicator value shall be understood as the value that indicates which pulse signal has the best quality. Depending on the chosen definition, this may be e.g. the lowest or the highest value of the quality indicator. Generally, various metrics can be used as quality indicators indicating a characteristic of the respective pulse signal. In one embodiment the signal-to-noise-ratio (SNR) (i.e. the height of the highest peak in a normalized spectrum) is used. In other embodiments, if the pulse is computed in different spatial locations (to further improve motion robustness), the SNR may be computed for all regions, but also the correlation between the different pulse signals (similarity matrix) may be used to determine together with the local SNRs a weighted mean pulse with a "weighted" SNR that is used as the "quality" indicator to decide which signature vector is the best.

The various units of the device 12 may be comprised in one or multiple digital or analog processors depending on how and where the invention is applied. The different units may completely or partly be implemented in software and carried out on a personal computer connected to one or more detectors. Some or all of the required functionality may also be implemented in hardware, e.g. in an application specific integrated circuit (ASIC) or in a field programmable gate array (FPGA).

Preferably, the pulse signal computation unit 32 uses a fixed set of different signature vectors $P_{bv}1$, $P_{bv}2$ and the processing unit 38 filters the time sequence of signature vectors that resulted in the pulse signal with the best quality indicator value Q1, Q2 to obtain a filtered signature vector from which the physiological information is derived. The fixed set of signature vectors $P_{bv}1$, $P_{bv}2$ cover the range of the vital sign to be measured. For instance, for SpO2, it may provide signature vectors corresponding to SpO2 values in a range between 60% and 100%. They are the same for every subject and may be stored indeed in a look-up table. However, if another blood gas is to be determined, other signature vectors are necessary (as this other gas gives a different blood-absorption spectrum, depending on the concentration of the gas). It is assumed here that only one blood component is to be determined, although, with a sufficiently high number of wavelengths, more than one blood component in principle is measureable, provided the set of signature vectors covers all possible combinations of gasses.

In other words, the above described processing is done over a time window, e.g. 10 seconds, of detection signals in each wavelength channel. This window is then sliding, i.e. the next measurement is again from a 10 seconds window, registered somewhat later in time. In the parallel option, every window yields an (e.g. SpO2) estimate (which is defined by the found "best" signature vector), and the succession of measurement results (signature vectors) gives a time sequence of measurements that can be (temporally) filtered in order to obtain a smoother and higher resolution measurement.

In an implementation of this embodiment quality indicator values are computed for only two fixed signature vectors. The relation between the two quality indicator values can then directly be translated into an SpO2 value.

In another implementation of this embodiment quality indicator values are computed for a broad range of signatures vectors suitable for the entire range of SpO2 values. In this implementation the best signature vector stands out immediately, meaning that this implementation can react to SpO2 changes without delay as it does not have to converge to it recursively.

Figure 4:
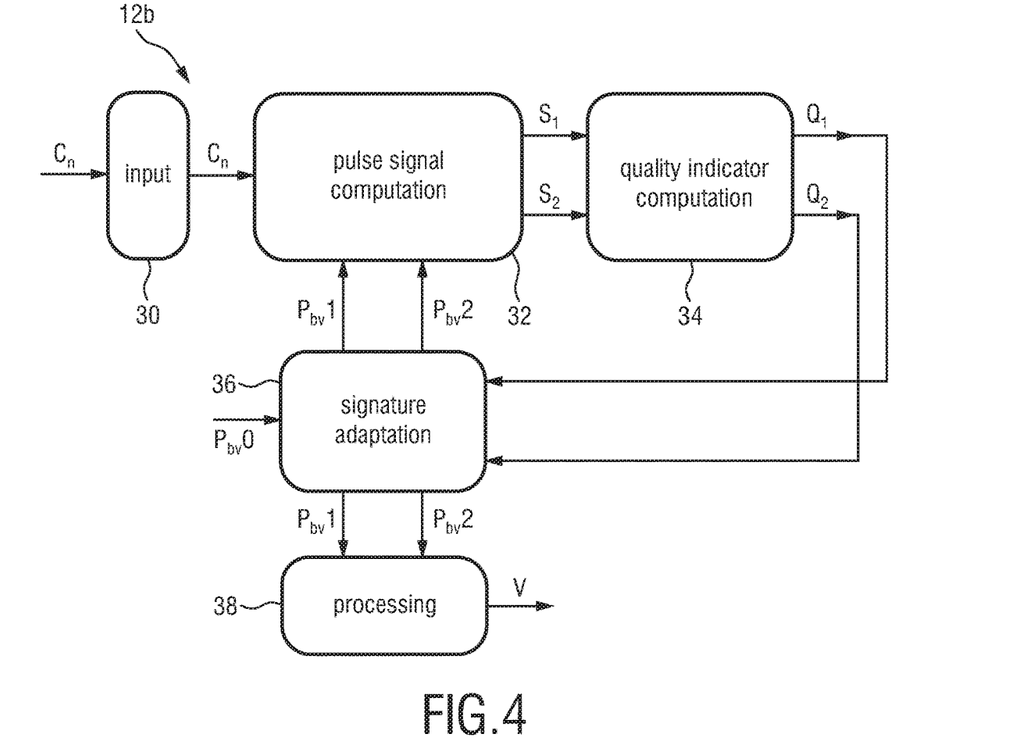
FIG. 4 shows a schematic diagram of a second embodiment of a device according to the present invention.

FIG. 4 shows a schematic diagram of a second embodiment 12b of a device 12 according to the present invention. In this embodiment a signature adaptation unit 36 is additionally provided for (iteratively/recursively) adapting one or more of the different signature vectors Pbv1, Pbv2 in a direction that depends on which pulse signal yields the best quality indicator value. The signature adaptation unit 36 is preferably configured to use a (predetermined) reference signature vector $P_{bv}0$ to obtain at least two signature vectors $P_{bv}1$, $P_{bv}2$ based on said quality indicator values Q1, Q2. Further, the pulse signal computation unit 32 is preferably configured to compute said pulse signals $S_1$, $S_2$ from said detection signal $C_n$ for said at least two signature vectors $P_{bv}1$, $P_{bv}2$ such that a pulse signal correlates with said at least two detection signals in a ratio determined by the corresponding signature vector. This ratio is defined by the above equation (1). It shows that the inner product (or correlation) of pulse signal S with each of the (normalized and DC-free) color channels in $C_n$ equals a multiple (arbitrary value k) times the signature vector $P_{BV}$. So the weights W are computed to realize this particular correlation ratio. This computation is shown in the above equation (2).

In each of the above embodiments it is possible to obtain a motion robust pulse signal using the basic method described in the above cited paper of de Haan and van Leest, or using the more elaborated version of that basic method described in the above cited paper of van Gastel et al. This paper describes the parallel computation of a pulse signal for many sub-regions, using the same signature vector ($P_{bv}$), and the successive combination of these parallel pulse signals (all based on a single signature vector) into the final pulse signal. The advantage of this approach is a further improved motion robustness of the pulse signal. Since it is still based on the basic $P_{bv}$-method, computing the final pulse signal with more than one $P_{bv}$-signature vector and then deciding which pulse signal has the highest quality can be used for SPO2, CO, Co2, etc. measurement. The basis is the same, it is just a bit more elaborate (multiple spatial sub-regions) to achieve a further improvement in motion-robustness.

Since the quality of this pulse signal depends on the correctness of the chosen signature vector $P_{bv}$, the pulse signal is computed for two (or more) different signature vectors $P_{bv}1$ and $P_{bv}2$. Consequently, the quality of the resulting pulse signal is judged. This can e.g. be achieved by computing the normalized (e.g. divided by the standard deviation) pulse signal over a time window, transforming it to the Fourier domain and defining a quality metric (i.e. quality indicator) as the amplitude of the highest peak in the range of the pulse frequencies. The higher this peak, the higher is the quality of the corresponding pulse signal considered. Two quality measures Q1 and Q2 are thus available, reflecting the quality of S1 and S2 respectively, which are used to adapt the signature vectors $P_{bv}1$ and $P_{bv}2$, used in the next time window. This can be done in a sliding window fashion, where the window shifts over one sample per computation cycle, but it is equally possible to slide the window faster, e.g. over 5 samples. An example window size is 200 samples for a sampling frequency of 20 Hz.

Alternatively, the quality of the resulting pulse signal may be judged by transforming it to the Fourier domain and defining a quality metric Q as the amplitude of the highest peak in the range of the pulse frequencies divided by the energy over the full frequency range (possibly excluding the peak). The higher this ratio, the higher is the quality of the pulse signal considered.

In another preferred embodiment, the quality indicators Q1 and Q2 are compared and their sign increases/decreases a counter. This counter value is used with an update vector U to compute $P_{bv}1$ and $P_{bv}2$ as: $\vec{P_{bv}1} = \vec{P_{bv}0}(\text{count}-1) \cdot U$ and $\vec{P_{bv}2} = \vec{P_{bv}0}(\text{count}+1) \cdot U$. If the update vector U is selected such that it morphs the signature for blood with 100% oxygenation in equal steps (of count value) to the signature for blood with 60% oxygenation, the resulting count value in the converged state is directly related to the SpO2 value of the subject under test. At the same time his/her pulse signal is obtained with the highest possible SNR as the signature is constantly adapted to the oxygenation level of the blood.

As the difference between $P_{bv}1$ and $P_{bv}2$ is not very large, the desired physiological information, e.g. SpO2, is mostly determined by the value of the counter that determines $P_{bv}1$ and $P_{bv}2$, i.e. either $P_{bv}1$ or $P_{bv}2$ can be used and both are derived from the counter value.

In an implementation, $P_{bv}0$ was selected as $[0.2\ 0.6\ 0.8]^T$ (reflecting the relative pulsatilities of 660 nm, 800 nm, and 840 nm, respectively) and the update vector U was selected as $[0.01\ 0\ -0.0036]^T$, which clearly shows that it is expected that the pulsatility of the 660 nm varies most, that of 840 nm about a factor of 3 less and in the opposite direction, while the pulsatility of the 800 nm channel is expected not to depend on SpO2.

It has further been recognized that the concept described in the above cited paper of de Haan and van Leest or the above cited paper of van Gastel et al has a clear optimal signature, visible in the quality metric Q, only in the presence of noise. This is because the algorithm aims at establishing a pulse signal that correlates with the color channels in the (by the $P_{bv}$) prescribed way. If the signature is a bit off, it will consequently mix in some noise signals to create a signal with the required signature. In the absence of noise (i.e. with an extremely stationary subject), the optimum may become very shallow. Therefore, in a further preferred embodiment some noise is added to the normalized color signals, prior to computing the weights to obtain the pulse signals. This noise preferably has a broad spectrum, or can be periodic but with a frequency outside the pulse-rate band. In these cases the quality indicator value calculation will be helped, as it computes the value of the highest frequency peak in the pulse-rate band of the normalized pulse signal (e.g. normalized by dividing over standard deviation of the pulse signal in a time window).

According to the embodiment illustrated in FIG. 4 the signature vector ($P_{bv}$), with which the best quality pulse signal can be computed, provides (in its coefficients) the relative pulsatilities of the different wavelength channels ($C_n$). The optimal signature vector, however, depends on the various substances in the blood (gasses like O2, CO2, CO, but also a substance like bilirubin). This is because these substances influence the absorption spectrum of the blood (e.g. the color of blood changes depending on oxygenation level). If an initial $P_{vb}$ vector is taken that corresponds e.g. to a healthy situation, like 100% oxygen saturation, then the update vector (in case it is aimed at estimation of the SpO2 value; it is different if bilirubin or CO, etc. shall be estimated), may be defined as a small step in the direction of the unhealthy situation (e.g. SpO2=60%). By adding a multiple of the update vector to the reference $P_{bv}$ vector, one arrives at $P_{bv}$ values reflecting anything between healthy and unhealthy oxygenation level, where the norm of the update vector determines the resolution with which all these levels can be approached.

By computing a pulse signal with all possible $P_{bv}$ vectors (all multiple updated $P_{bv}$s) from the channels $C_n$, as done with the embodiment shown in FIG. 3, there will be one particular pulse signal that has the best SNR. This $P_{bv}$ then identifies the actual SpO2 (CO, bilirubin, etc.). Instead of testing all of them, it is also possible to test just two (or a small number), as done with the embodiment shown in FIG. 4, and modify the test set (i.e. the set of $P_{bv}$s) until the system starts oscillating around the optimal value. This describes the iterative approach, where the method continues until convergence is reached). Alternatively, just a single update can be made, and then the processing time window can be shifted to do the next single update. This is the recursive option. Since the SpO2 value does not change rapidly, this recursive approach is efficient, and reaches convergence after a couple of seconds. The oscillations can be removed with a low pass filter to obtain a more accurate measurement. The filtering allows a relative large update (fast convergence) with large oscillation, which because of the temporal low-pass filtering does not sacrifice accuracy.

In case all of the signature vectors are tested, but a relatively large update vector is used (i.e. a sparse sampling of the space between healthy and unhealthy is performed), this parallel system will also likely hesitate between two (or more) optimal $P_{bv}$s (certainly if the sampling is very sparse) and again a temporal low-pass filter may eliminate the noise from this hesitation and thus provide an increased accuracy compared to the sparse sampling.

In an embodiment a robust pulse signal measurement has been implemented with a detector sampling the spectrum around 650 nm, 810 nm and 900 nm. In an alternative embodiment, 760 nm, 800 nm and 840 nm are used. In yet an alternative embodiment, more suitable for bilirubin detection, 475 nm, 550 nm and 650 nm may be used. Finally, it is equally possible to use only two wavelengths, e.g. 650 nm and 800 nm, or use four (e.g. 660 nm, 760 nm, 800 nm, and 860 nm), or even more wavelengths to more accurately capture the signature of the blood volume pulse $P_{bv}$ and optionally determine the concentration of more than one blood gas in one measurement.

In the above, the embodiments have been described with the assumption to determine SpO2. The invention can also be applied for determining other physiological information, such as bilirubin, CO or CO2. The absorption curves (as function of wavelength) of blood with different fractions of bilirubin, CO or CO2 differ from the curves for different values of SpO2. As a consequence the update vector has to be a different one (the initial vector may be the one of 97% SpO2 (with 0% bilirubin, 0% CO, 0% CO2), but the proposed method generally tracks only one variable fraction (O2, CO, CO2 or bilirubin) assuming the other fractions to be known and stable). To measure more fractions simultaneously, more wavelength channels are necessary to disambiguate the measurement.

Figure 5A:
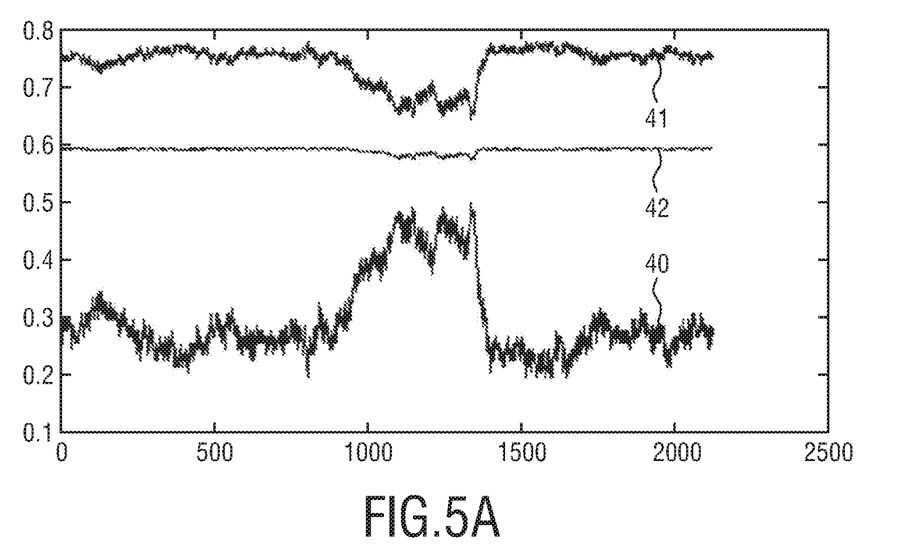
FIGS. 5A and 5B show diagrams of the blood volume pulse vector at different wavelengths and the resulting SpO2 estimate over time respectively.
Figure 5B:
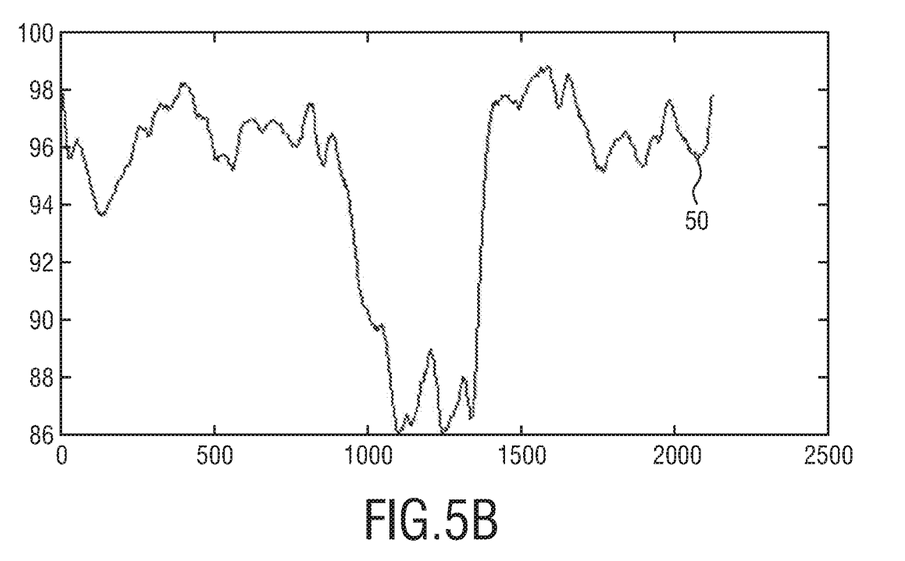

The device according to the present invention has been implemented and tested for a person who holds his breath during a period of time to induce an SpO2 dip. The resulting SpO2 value obtained with this method is shown in FIG. 5. FIG. 5A shows how the blood volume pulse vector evolves during the experiment (with relative pulsatilities of 660 nm (curve 40), 810 nm (curve 41) and 840 nm (curve 42). FIG. 5B shows the resulting SpO2 estimate 50 derived from the count value that adapts the test signatures $P_{bv}1$ and $P_{bv}2$. The SpO2 dip during breath holding is clearly perceived.

In a second experiment the robustness of the device according to the present invention has been demonstrated for strong subject motion. To this end a recording of a subject exercising on a stationary bike in a fitness setting was made. The camera is a regular RGB color camera sampling the spectrum around 450 nm (curve 60 in FIG. 6), 550 nm (curve 61), and 650 nm (curve 62).

Figure 6:
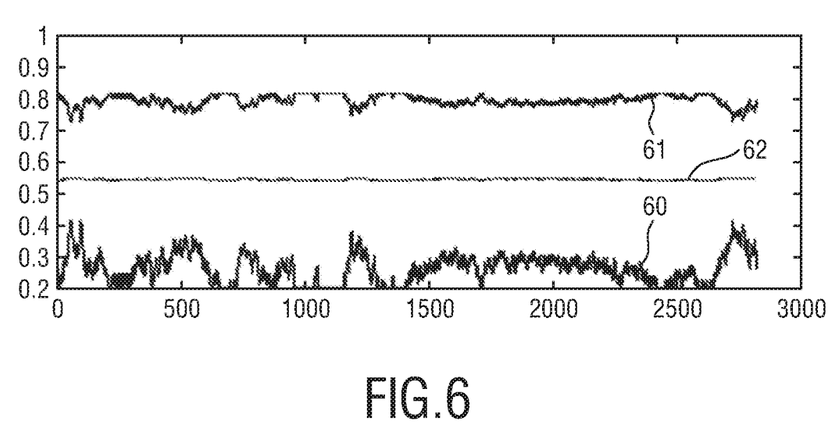
FIG. 6 shows a diagram of the blood volume pulse vector at different wavelengths for an exercising subject.

Although, in this case as illustrated in FIG. 6, the variations in the signature vector cannot be translated into an SpO2 estimate (the RGB camera is not calibrated for SpO2), it can be seen that the relative pulsatilities from the resulting signature vector remain quite stable. This is a great improvement to known methods for SpO2 measurement that all confuse the vigorous motion with the actual PPG signal and hence decide that pulsatilities are identical in all channels (due to motion). According to this experiment it was expected that the blood volume vector stays rather stable in comparison with the experiment illustrated in FIG. 5, where a subject holds his breath.

In a final experiment the same configuration as used in the first experiment was used on 10 healthy subjects. Although the obtained SpO2 values showed some noise, all obtained values were between 95 and 99% oxygenation, giving initial confidence that calibratability of the described method should be feasible.

The above described methods have mainly been explained with respect to contactless sensors. Generally, the same methods can also be used for contact sensors. By way of example, the present invention can be applied in the field of health care, e.g. unobtrusive remote patient monitoring, general surveillances, security monitoring and so-called lifestyle environments, such as fitness equipment, or the like. Applications may include monitoring of oxygen saturation (pulse oximetry), heart rate, blood pressure, cardiac output, changes of blood perfusion, assessment of autonomic functions, and detection of peripheral vascular diseases. The present invention can e.g. be used for rapid and reliable pulse detection of a critical patient, for instance during automated CPR (cardiopulmonary resuscitation). The system can be used for monitoring of vital signs of neonates as well. In summary, the present invention improves the SNR considerably for near stationary subjects and consequently leads to a more accurate beat-to-beat measurement.

According to an embodiment the present invention presents a device (and a corresponding method) for extracting physiological information indicative of at least one vital sign of a subject, said device comprising:

an input interface configured to obtain at least two detection signals derived from detected electromagnetic radiation transmitted through or reflected from a skin region of a subject, wherein each detection signal comprises wavelength-dependent reflection or transmission information in a different wavelength channel, a pulse signal computation unit configured to compute at least two pulse signals from said at least two detection signals using different signature vectors for the computation of each pulse signal, a quality indicator computation unit configured to compute quality indicator values for said pulse signals indicating a characteristic of the respective pulse signal, and a processing unit configured to derive physiological information indicative of at least one vital sign from the signature vector that results in the pulse signal with the best quality indicator value and/or from said pulse signal.

Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible device or apparatus that can contain, store, communicate, propagate, or transport the program for use by or in connection with the instruction execution device.

In so far as embodiments of the disclosure have been described as being implemented, at least in part, by software-controlled data processing devices, it will be appreciated that the non-transitory machine-readable medium carrying such software, such as an optical disk, a magnetic disk, semiconductor memory or the like, is also considered to represent an embodiment of the present disclosure.

The computer usable or computer readable medium can be, for example, without limitation, an electronic, magnetic, optical, electromagnetic, infrared, or semiconductor system, or a propagation medium. Non-limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk—read only memory (CD-ROM), compact disk—read/write (CD-R/W), and DVD.

Further, a computer usable or computer readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example, without limitation, physical or wireless.

A data processing system or device suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories, which provide temporary storage of at least some computer readable or computer usable program code to reduce the number of times code may be retrieved from bulk storage during execution of the code.

Input/output, or I/O devices, can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems, remote printers, or storage devices through intervening private or public networks. Non-limiting examples are modems and network adapters and are just a few of the currently available types of communications adapters.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different advantages as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

The invention claimed is:

1. A device for extracting physiological information indicative of at least one vital sign of a subject, said device comprising:
at least one interface configured to obtain at least two detection signals derived from detected electromagnetic radiation transmitted through or reflected from a skin region of a subject, wherein each detection signal comprises wavelength-dependent reflection or transmission information in a different wavelength channel,
a pulse signal computation unit configured to compute at least two pulse signals $S_1$, $S_2$ from said at least two detection signals using a plurality of signature vectors which are different from each other for the computation of each of the pulse signals, said signature vectors providing relative pulsatility of a respective pulse signal of the at least two detection signals caused by the light dependent reflection or transmission information, wherein the computation of the at least two pulse signals involves computing a weighted combination of the at least two detection signals to generate each respective pulse signal, wherein products with the at least two detection signals equal the relative pulsatilities as represented by the respective signature vector,
a quality indicator computation unit configured to compute a quality indicator value for each of the at least two pulse signals indicating a characteristic of each of the at least two pulse signals,
a control signal computation unit configured to compute a control signal CS from said quality indicator values,
a signature adaptation unit configured to compute the plurality of signature vectors by adding update vectors (CS−1)·$\vec{U}$ or (CS+1)·$\vec{U}$ to a reference signature vector ($P_{bv}0$), and to adapt one or more of the plurality of signature vectors in a direction that depends on a one of the at least two pulse signals that yields the best quality indicator value, and to adapt said reference signature vector ($P_{bv}0$) based on said control signal CS to obtain the plurality of signature vectors,
the pulse signal computation unit configured to compute said at least two pulse signals from said at least two detection signals for said plurality of signature vectors such that the one of the at least two pulse signals that correlates with said at least two detection signals in a ratio determined by a one of the signature vectors corresponding to the one of the at least two pulse signals and to increase the control signal CS in case the quality indicator value of a second of the at least two pulse signals is larger than the quality indicator value of a first of the at least two pulse signals and vice versa, and
a processing unit configured to derive physiological information indicative of at least one vital sign from at least one of the plurality of signature vectors that results in the one of the at least two pulse signals with the best quality indicator value or from said one of the at least two pulse signals, the physiological information indicative of the at least one vital sign being sent to the at least one interface for communication to a user.

2. The device as claimed in claim 1, wherein the plurality of signature vectors includes a fixed set of signature vectors and said processing unit is configured to filter a time sequence of the fixed set of signature vectors, the one of the pulse signals with the best quality indicator value being used as a filtered signature vector from which the physiological information is derived.

3. The device as claimed in claim 1, wherein the reference signal vector adapted by said signature adaptation unit is a reference normalized blood volume pulse vector.

4. The device as claimed in claim 1, wherein said quality indicator computation unit is configured to compute a spectrum of each of the at least two pulse signals and to use an amplitude of a highest peak in a range as the quality indicator for each of the at least two said pulse signals.

5. The device as claimed in claim 4, wherein said quality indicator computation unit is configured to compute the spectrum of each of the at least two pulse signals over a sliding time window and to use the amplitude of the highest peak in a range of typical pulse frequencies as the quality indicator for each of the at least two pulse signals.

6. The device as claimed in claim 1, wherein said quality indicator computation unit is configured to compute the at least two pulse signals in a sliding time window and to define an amplitude of a highest peak in a range of the pulse frequencies of a spectrum, divided by an energy over a full frequency range, as the quality indicator for each of the at least two pulse signals.

7. A device for extracting physiological information indicative of at least one vital sign of a subject, said device comprising a processor configured to:
receive from an interface at least two detection signals derived from detected electromagnetic radiation transmitted through or reflected from a skin region of a subject, wherein each detection signal comprises wavelength-dependent reflection or transmission information in a different wavelength channel,
compute at least two signature vectors based on a reference signature vector ($P_{bv}0$),
compute a plurality of pulse signals from said at least two detection signals using that at least two signature vectors for the computation of each pulse signal from the at least two detection signals wherein each of the at least two signature vectors is different, each of said at least two signature vectors representing expected relative pulsatilities of a corresponding one of the pulse signals, wherein the computation of each of the pulse signals involves a weighted combination of the at least two detection signals using weights resulting in pulse signals for which products with the corresponding detection signals equals the expected relative pulsatility represented by the corresponding signature vector,
compute quality indicator values for each of the pulse signals indicating a characteristic of the corresponding one of the pulse signals,
adapt one or more of the at least two signature vectors in a direction that depends on a one of the at least two pulse signals that yields the best quality indicator value,
select at least one of the plurality of signature vectors based on the quality indicator values;
derive physiological information indicative of at least one vital sign from the selected at least one of the plurality of signature vectors that results in a one of the pulse signals with the best quality indicator value or from said pulse signal, and
transfer the physiological information to the interface for communication to a clinician,
wherein said at least two pulse signals are computed from said at least two detection signals for said at least two signature vectors such that the one of the at least two pulse signals that correlates with said at least two detection signals in a ratio determined by a one of the signature vectors corresponding to the one of the at least two pulse signals, wherein computing the at least two signature vectors includes comparing said quality indicator values, increasing or decreasing a counter value depending on a sign of the comparison and using the counter value together with a predetermined update vector and the reference signature vector ($P_{bv}0$).

8. The device as claimed in claim 1, wherein said pulse signal computation unit is configured to add noise to one or more normalized and DC-free detection signals before computing said at least two pulse signals therefrom.

9. The device as claimed in claim 1, wherein said pulse signal computation unit is configured to compute said at least two pulse signals $S_1$, $S_2$ by computing a covariance matrix $Q = C_n C_n^T$ of normalized DC-free detection signals $C_n$ over a time window and find the weights $W_x$ to compute a pulse signal $S_x = \vec{W}_x C_n$ as $\vec{W}_x = k\vec{P}_{bvx} Q^{-1}$, where k is chosen to make $\|\vec{W}_x\| = 1$ and $x \in \{1, 2\}$.

10. A system for extracting physiological information indicative of at least one vital sign of a subject, said system comprising:
   a detector configured to detect electromagnetic radiation transmitted through or reflected from a skin region of a subject and to derive at least two detection signals from the detected electromagnetic radiation, wherein each detection signal comprises wavelength-dependent reflection or transmission information in a different wavelength channel,
   a device as claimed in claim 1 for extracting physiological information; and
   a display device configured to display the extracted physiological information.

11. A method for extracting physiological information indicative of at least one vital sign of a subject, said method comprising:
   obtaining at least two detection signals derived from detected electromagnetic radiation transmitted through or reflected from a skin region of a subject, wherein each detection signal comprises wavelength-dependent reflection or transmission information in a different wavelength channel,
   computing at least two pulse signals, each of the at least two pulse signals being computed from said at least two detection signals, each of the pulse signals being computed using different ones of a plurality of signature vectors, each of the signature vectors providing an expected relative pulsatility of a corresponding one of the at least two pulse signals, wherein the computation of each of the at least two pulse signals involves a weighted combination of the at least two detection signals using weights selected such that each of the at least two pulse signals correlates with the at least two detection signals as represented by the respective signature vector,
   computing quality indicator values for each of said at least two pulse signals indicating a characteristic of each of the at least two pulse signals,
   computing a control signal CS from the quality indicator values,
   computing the plurality of signature vectors by adding update vectors $(CS-1) \cdot \vec{U}$ and $(CS+1) \cdot \vec{U}$ to a reference signature vector ($P_{bv}0$),
   adapting one or more of the plurality of signature vectors in a direction that depends on a one of the at least two pulse signals that yields the best quality indicator value,
   adapting the reference signature vector ($P_{bv}0$) based on the control signal CS to obtain the plurality of signature vectors,
   computing the at least two pulse signals from the at least two detection signals for the plurality of signature vectors such that the one of the at least two pulse signals that correlates with the at least two detection signals in a ratio determined by a one of the signature vectors corresponding to the one of the at least two pulse signals, and
   increasing the control signal CS in case the quality indicator value of the second of the at least two pulse signals is larger than a quality indicator value of a first of the at least two pulse signals and vice versa,
   deriving physiological information indicative of at least one vital sign from the signature vector that results in a one of the pulse signals with the best quality indicator value or from said one of the pulse signals with the best quality indicator value, and
   communicating the physiological information to a user.

12. A non-transitory computer-readable recording medium that stores therein a computer program product, which, when executed by a processor, causes the method as claimed in claim 11 to be performed.

13. A device for extracting physiological information indicative of at least one vital sign of a subject, said device comprising a processor configured to:
   receive from an interface at least two detection signals derived from detected electromagnetic radiation transmitted through or reflected from a skin region of a subject, wherein each detection signal comprises wavelength-dependent reflection or transmission information in a different wavelength channel,
   compute a plurality of pulse signals from said at least two detection signals using a plurality of signature vectors for the computation of each pulse signal from the at least two detection signals wherein each of the plurality of signature vectors is different, each of said signature vectors representing expected relative pulsatilities of a corresponding one of the pulse signals, wherein the computation of each of the pulse signals involves a weighted combination of the at least two detection signals using weights resulting in pulse signals for which products with the corresponding detection signals equals the expected relative pulsatility represented by the corresponding signature vector,
   compute quality indicator values for each of the pulse signals indicating a characteristic of the corresponding one of the pulse signals,
   compute a control signal CS from the quality indicator values,
   compute the plurality of signature vectors by adding update vectors $(CS-1) \cdot \vec{U}$ and $(CS+1) \cdot \vec{U}$ to a reference signature vector ($P_{bv}0$),
   adapt one or more of the plurality of signature vectors in a direction that depends on a one of the at least two pulse signals that yields the best quality indicator value,
   adapt the reference signature vector ($P_{bv}0$) based on the control signal CS to obtain the plurality of signature vectors,
   compute the plurality of pulse signals from the at least two detection signals for the plurality of signature vectors such that the one of the plurality of pulse signals that correlates with the at least two detection signals in a ratio determined by a one of the signature vectors corresponding to the one of the plurality of pulse signals, and increase the control signal CS in case the quality indicator value of the second of the plurality of pulse signals is larger than a quality indicator value of a first of the plurality of pulse signals and vice versa, select at least one of the plurality of signature vectors based on the quality indicator values;

derive physiological information indicative of at least one vital sign from the selected at least one of the plurality of signature vectors that results in a one of the pulse signals with the best quality indicator value or from said pulse signal, and transfer the physiological information to the interface for communication to a clinician.

14. The device as claimed in claim 13, wherein the plurality of signature vectors comprises a fixed set of signature vectors and wherein the physiological information is derived from a one of the fixed set of signature vectors that results in a one of the pulse signals with a best quality indicator value.

15. The device as claimed in claim 13, wherein computing the signature vectors includes:
  a) selecting a reference signature vector,
  b) from the reference signature vector, generating first and second signature vectors,
  c) determine which of the first and second signature vectors results in the one of the pulse signals having the best quality indicator value,
  d) taking the one of the first and second signature vectors that results in the one of the pulse signals having the best quality indicator value as the reference signature vector and repeating steps a)-c) to obtain an iteratively optimized signature vectors for deriving the physiological information.

* * * * *